(12) United States Patent
Sudo

(10) Patent No.: US 7,067,270 B2
(45) Date of Patent: Jun. 27, 2006

(54) METHOD FOR DETECTING PROTEIN

(75) Inventor: Yukio Sudo, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 11/008,954

(22) Filed: Dec. 13, 2004

(65) Prior Publication Data

US 2005/0196815 A1    Sep. 8, 2005

(30) Foreign Application Priority Data

Dec. 12, 2003   (JP) ............................... 2003-415269

(51) Int. Cl.
| | |
|---|---|
| G01N 33/533 | (2006.01) |
| G01N 33/532 | (2006.01) |
| G01N 33/535 | (2006.01) |
| G01N 33/543 | (2006.01) |
| G01N 33/545 | (2006.01) |

(52) U.S. Cl. ..................... 435/7.95; 436/546; 436/518; 436/530; 436/531; 436/524; 436/544; 530/388.9

(58) Field of Classification Search .............. 435/7.1, 435/7.72, 7.95; 436/544, 518, 546, 530, 436/531, 524; 530/388.9; 544/271, 274
See application file for complete search history.

(56) References Cited

U.S. PATENT DOCUMENTS

| 4,378,428 A | * | 3/1983 | Farina et al. ............. 435/7.23 |
| 4,469,797 A | | 9/1984 | Albarella |
| 5,198,537 A | | 3/1993 | Huber et al. |

FOREIGN PATENT DOCUMENTS

WO    WO 96/03423 A1    2/1996

OTHER PUBLICATIONS

Ed Harlow, et al., "Antibodies A Laboratory Manual," Cold Spring Harbor Laboratory, pp. 53-138, 1988.

* cited by examiner

*Primary Examiner*—Long V. Le
*Assistant Examiner*—Shafiqul Haq
(74) *Attorney, Agent, or Firm*—Sughrue Mion, PLLC

(57) ABSTRACT

An object of the present invention is to provide a method for detecting a protein using a nonradioactive label which is prevented to a smaller extent than in the case of the interaction of biotin/(strepto)avidin, and which achieves higher detection sensitivity than that of the detection system using DIG. The present invention provides a method for detecting a target substance, which comprises steps of: (A) allowing a target substance to come into contact with a protein labeled with a compound having a 6-membered ring, so as to carry out a binding reaction; and (B) detecting the protein labeled with the compound having a 6-membered ring, which was bound to the target substance, by using an antibody against the above compound having a 6-membered ring.

9 Claims, No Drawings

METHOD FOR DETECTING PROTEIN

TECHNICAL FIELD

The present invention relates to a method for detecting a small amount of a target substance.

BACKGROUND ART

A previously known method for detecting a protein comprises steps of allowing an antibody specifically binding to a protein immobilized on a carrier for immobilization such as a membrane, and being radiolabeled with a radioisotope, to react with the protein; removing an unreacted labeled antibody portion by washing; and detecting the residual radiolabel, so as to detect the protein.

Such a detection method using a radiolabeled antibody is useful in that it allows for high sensitivity. However, it requires special equipment for treating radioactive compounds, and thus, it is hard to deal with. Moreover, the method is also problematic regarding disposal of radioactive substances. Furthermore, since a radioactive substance has a half-life, a radiolabeled antibody can be used only for a certain period of time after production thereof. Further, when the amount of DNA to be detected is small, this detection method requires a long period of time (several days to several weeks) as an exposure time for the autoradiography. In order to solve these problems, a nonradioactive detection method has been developed.

For example, there has been known a method of using an antibody into which a biotin molecule is introduced, wherein the biotin molecule of the antibody which was bound to a target substance is detected by using a (strepto)avidin-labeled enzyme complex. A protein can be detected with relatively high sensitivity in this detection system via biotin/(strepto)avidin. However, this method has disadvantages in that biotin, which is vitamin, is often generated in a biological sample, and the interaction of biotin/(strepto)avidin is thereby likely to be prevented during detection.

Japanese Patent Laid-Open (Kokai) No. 1-215300 describes a detection system using digoxigenin (DIG). In this detection system, digoxigenin is used as a label binding to an antibody. To detect the label, an anti-digoxigenin antibody to which alkaline phosphatase was bound is allowed to bind to digoxigenin, and thereafter, the label is detected by color development of a substrate as a result of the catalytic reaction of the alkaline phosphatase.

In the aforementioned detection system using DIG however, an antibody against a target substance is labeled with DIG However, a DIG derivative has disadvantages in that it is poor in water solubility and it is difficult to achieve efficient labeling of an antibody therewith.

DISCLOSURE OF THE INVENTION

It is an object of the present invention to solve the aforementioned problems of the prior art techniques. That is to say, it is an object of the present invention to provide a method for detecting a protein using a nonradioactive label which is prevented to a smaller extent than in the case of the interaction of biotin/(strepto)avidin, and which achieves higher detection sensitivity than that of the detection system using DIG.

As a result of intensive studies directed towards achieving the aforementioned objects, the present inventors have found that a protein labeled with a compound having a 6-membered ring represented by the formula (1) defined in the present specification is allowed to bind to a target substance, and thereafter the protein labeled with the above compound having a 6-membered ring is detected by using an antibody against the above compound having a 6-membered ring, so that the target substance can efficiently be detected with high sensitivity, thereby completing the present invention.

Thus, the present invention provides a method for detecting a target substance, which comprises steps of:
(A) allowing a target substance to come into contact with a protein labeled with a compound having a 6-membered ring represented by the following formula (1), so as to carry out a binding reaction; and
(B) detecting the protein labeled with the compound having a 6-membered ring, which was bound to the target substance, by using an antibody against the above compound having a 6-membered ring,

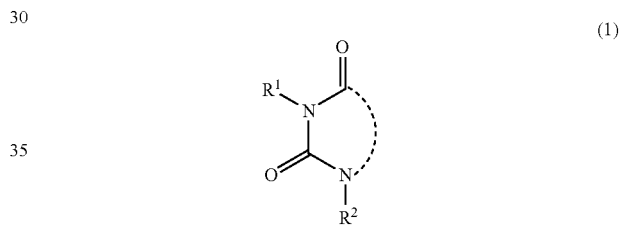

(1)

wherein $R^1$ and $R^2$ may be identical or different, and may independently represent a hydrogen atom, or alkyl group containing 1 to 6 carbon atoms, and the dotted line represents an atomic group necessary for forming a 6-membered ring.

In the first embodiment of the present invention, a target substance is detected by using a labeled antibody as an antibody against the compound having a 6-membered ring, and detecting a protein bound to the target substance, which is labeled with the compound having a 6-membered ring.

In the second embodiment of the present invention, a target substance is detected by using an antibody against the compound having a 6-membered ring and a labeled antibody capable of specifically binding to the above antibody, and detecting a protein bound to the target substance, which is labeled with the compound having a 6-membered ring.

Preferably, the target substance is immobilized on a solid phase carrier.

Preferably, the compound having a 6-membered ring represented by the formula (1) is a theophylline derivative or a phenobarbital derivative.

Preferably, the compound having a 6-membered ring represented by the formula (1) is a compound represented by the following formula:

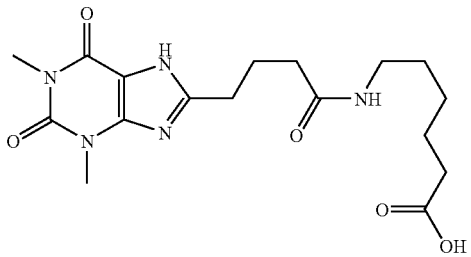

Theophylline-LC

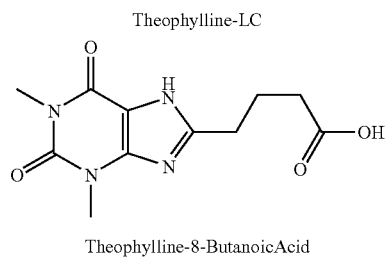

Theophylline-8-ButanoicAcid

Preferably, the antibody against the compound having a 6-membered ring is a monoclonal antibody.

Preferably, enzyme labeling, fluorescent labeling, chemoluminescent labeling or bioluminescent labeling is used as the label of a labeled antibody.

Preferably, alkaline phosphatase, peroxidase, β-galactosidase, acetate kinase, luciferase, amylase, glucose-6-phosphate dehydrogenase, cellulase, or xanthine oxidase is used as a labeling enzyme for the labeled antibody.

Preferably, the detection method is the luminescence method, the fluorescence method, the delayed fluorescence method, the colorimetric method, or the electrochemical method.

Preferably, the protein labeled with the compound having a 6-membered ring is an antibody against the target substance, a receptor, a DNA-binding protein, or a fragment thereof.

BEST MODE FOR CARRYING OUT THE INVENTION

The embodiments of the present invention will be described in detail below.

In the present invention, a target substance is first allowed to come into contact with a protein labeled with a compound (which may be referred to as a hapten in the present specification) having a 6-membered ring represented by the following formula (1), so as to carry out a binding reaction:

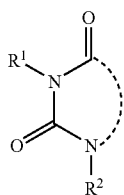

(1)

wherein $R^1$ and $R^2$ may be identical or different, and may independently represent a hydrogen atom, or alkyl group containing 1 to 6 carbon atoms, and the dotted line represents an atomic group necessary for forming a 6-membered ring.

Examples of an alkyl group containing 1 to 6 carbon atoms represented by $R^1$ or $R^2$ may include methyl, ethyl, propyl, butyl, pentyl, and hexyl. These may be either straight chains or branched chains.

An atomic group necessary for forming a 6-membered ring, which is indicated with the dotted line in the formula (1), may be an atomic group, the main chain of which is composed of carbon atoms or heteroatoms forming a hetero ring (e.g. nitrogen atoms, oxygen atoms, or sulfur atoms). That is to say, the main chain of the atomic group is a connecting group consisting of two atoms selected from carbon atoms or heteroatoms (e.g. nitrogen atoms, oxygen atoms, or sulfur atoms). Moreover, hydrogen atoms or substituents is bound to these carbon atoms or heteroatoms, so as to maintain an appropriate valence. Furthermore, a double bond may exist in the atomic group.

Specific examples of an atomic group necessary for forming a 6-membered ring, which is indicated with the dotted line in the formula (1), may include, but are not limited to, $-CR^{11}R^{12}-CR^{13}R^{14}-$, $-CR^{11}=CR^{13}-$, $-CR^{11}R^{12}-NR^{13}-$, $-CR^{11}=N-$, $-NR^{11}-NR^{13}-$, $-N=N-$, $-CR^{11}R^{12}-O-$, $-CR^{11}R^{12}-S-$, $-NR^{11}-O-$, and $-NR^{11}-S-$.

Each of $R^{11}$, $R^{12}$, $R^{13}$, and $R^{14}$ independently represents a hydrogen atom or substituent. The type of such a substituent is not particularly limited, and any substituent may be used. Examples of a substituent may include a halogen atom (fluorine, chlorine, bromine, iodine), an alkyl group containing 1 to 10 carbon atoms, an alkenyl group containing 1 to 10 carbon atoms, alkynyl group containing 1 to 10 carbon atoms, an aryl group containing 6 to 20 carbon atoms, and an alkoxy group containing 1 to 10 carbon atoms. Moreover, $R^{11}$ and $R^{12}$, or $R^{13}$ and $R^{14}$ may be combined together to form a ketone group (=O).

An atomic group which provides a theophylline derivative or a phenobarbital derivative as the compound represented by the formula (1), is preferable as the present atomic group.

In order that the compound represented by the formula (1) can be a theophylline derivative, the present atomic group should be represented by $-C(NHR^{21})=C(N=R^{22})-$ wherein $R^{21}$ and $R^{22}$ are combiner together to form a 5-membered ring.

In order that the compound represented by the formula (1) can be a phenobarbital derivative, the present atomic group should be represented by $-C(=O)-C(CH_2CH_3)(C_6H_5)-$.

The compound having a 6-membered ring represented by the formula (1) may directly bind to a protein (capable of binding to a target substance), but it preferably binds to the protein via a linker. It is preferable that an atomic group necessary for forming a 6-membered ring indicated with the dotted line in the formula (1) is used as a linker-binding site of the compound having a 6-membered ring represented by the formula (1).

A linker should have a certain length, which is necessary for preventing what is called a steric hindrance occurring during a hapten-antibody reaction. For example, a linker preferably has a length of 4 or more atoms.

Specific examples of the compound having a 6-membered ring represented by the formula (1) to which a linker was bound may include theophylline-LC and theophylline-8-butanoic acid, the structures of which are shown below.

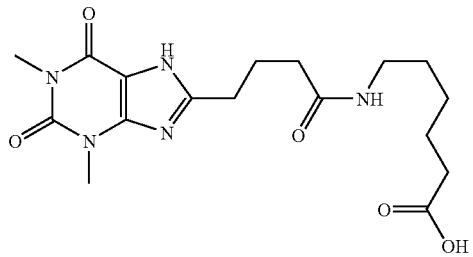

Theophylline-LC

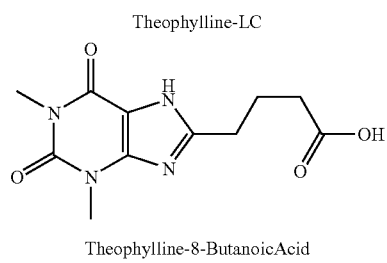

Theophylline-8-ButanoicAcid

The term a "protein labeled with a compound having a 6-membered ring" used herein means all types of proteins and peptides capable of specifically binding to a target substance. Most preferred examples of such a protein may include an antibody against the target substance, a part thereof, and a fragment thereof. When the target substance is a ligand, examples of such a protein may also include a receptor specifically binding to the ligand and a fragment thereof. When the target substance is nucleic acid, examples of such a protein may also include a protein and a peptide (aptamer), which specifically binds to the nucleic acid.

When the compound having a 6-membered ring in the present invention is used to label a protein or peptide compound capable of binding to a target substance, it may be bound to the protein or peptide compound via an $NH_2$ group, COOH group, SH group, or the like. As such a labeling method, the method described in *Koso Meneki Sokutei Ho* (Enzyme Immunoassay), Igaku-Shoin Ltd., 1987, and the like can be applied.

In the present invention, a target substance is allowed to come into contact with a protein labeled with a compound having a 6-membered ring represented by the formula (1) defined in the present specification, so as to carry out a binding reaction. The target substance is preferably a protein immobilized on a solid carrier.

In the method of the present invention, when a target substance is immobilized on a solid carrier, various types of known carriers for immobilization are used as solid carriers for immobilizing the target substance. In general, a material, which has a form of being easily immersed in a solution for a hapten-antibody reaction and has low nonspecific binding properties with an antibody or protein causing background, is used as a solid carrier. Specific examples of such a solid carrier may include a nitrocellulose filter, a nylon filter, a plastic, Plexiglas, and a plastic or Plexiglas coated with nitrocellulose, quartz or nylon.

As stated above, in the present invention, a target substance is preferably immobilized on the surface of a solid carrier. Immobilization can be carried out according to common methods. For example, a solution containing a target substance is spotted on a solid carrier such as a nylon membrane, followed by air-drying. Thereafter, blocking is preferably carried out using a BSA solution or the like.

Subsequently, the solid carrier is treated with a solution containing a protein labeled with a compound having a 6-membered ring represented by the formula (1), so that the target substance is allowed to come into contact with the protein, so as to carry out a binding reaction. The binding reaction can be carried out according to common methods. For example, when such a binding reaction is an antigen-antibody reaction, a solid carrier to which an antigen was bound is shaken in an antibody solution containing 0.5% BSA, so as to carry out a binding reaction. After completion of the above binding reaction, a protein bound to the target substance is detected by using an antibody against the above compound having a 6-membered ring.

The antibody against the above compound having a 6-membered ring used in the present invention (that is, an anti-hapten antibody) is produced by using, as an antigen, the above compound having a 6-membered ring, which is a hapten. It may be either a polyclonal antibody or monoclonal antibody. A method of producing a polyclonal antibody or monoclonal antibody, using a hapten as an antigen, is well known. Thus, such antibodies can be obtained according to known methods. Examples of an animal used to produce a polyclonal antibody may include a rabbit, a Guinea pig, and a mouse. It is of course also possible to use an antibody produced by genetic engineering, or a fragment thereof.

In the first embodiment of the present invention, the above antibody is bound to a label which is used to detect the antibody. An example of such a label may be an enzyme, such as an enzyme causing a color reaction, luminescence reaction or fluorescence reaction. Examples of an enzyme causing a color reaction may include alkaline phosphatase, β-galactosidase, and peroxidase. Examples of an enzyme causing a luminescence reaction may include luciferase and peroxidase. Examples of an enzyme causing a fluorescence reaction may include alkaline phosphatase, peroxidase, and esterase. In order to detect these enzymes, a colorimetric substrate, a luminescent substrate, a fluorescent substrate and the like are used depending on the type of an enzyme. An enzyme and a substrate used in detection, a detection reaction, and the like can be determined according to common methods.

In the second embodiment of the present invention, an anti-hapten antibody (a primary antibody) can be detected by using a labeled antibody (a secondary antibody) against the anti-hapten antibody, without directly labeling the anti-hapten antibody. For example, when a certain type of animal antibody is used as an anti-hapten antibody (a primary antibody), another type of antibody (a secondary antibody) specifically binding to the above animal antibody can be used. For example, when a mouse antibody is used as a primary antibody (an anti-hapten antibody), a rabbit antibody specific to the mouse antibody can be used as a secondary antibody.

In this embodiment, a label to be bound to the secondary antibody to detect it, and a detection method thereof, are the same as in the case of detecting an anti-hapten antibody in the first embodiment. Natural antibodies may directly be used as the aforementioned primary antibody and/or secondary antibody. Otherwise, antibody fragments having binding properties, such as F(ab)$_2$ or F(ab), may also be used. Fragmentation of these antibodies can be carried out according to common methods.

A protein bound to a target substance, which is labeled with a compound having a 6-membered ring, can be detected by using the aforementioned anti-hapten antibody according to common methods.

In the first embodiment of the present invention, a hapten contained in a protein labeled with a compound (hapten) having a 6-membered ring is allowed to bind to a labeled anti-hapten antibody. This reaction can be carried out under ordinary conditions. For example, the reaction can be carried out in Tris buffer solution (pH 7.5) or phosphate buffer solution at a temperature between 20° C. and 37° C. for 15 to 60 minutes. Subsequently, a solid carrier is washed with a washing solution such as Tris buffer solution (pH 7.5) to remove an unreacted labeled antibody. Thereafter, if a label for the anti-hapten antibody is an enzyme, the enzyme is allowed to react with a color substrate against the enzyme, so that color development is carried out.

As a reaction medium in this case, Tris buffer solution (pH 7.5) is used, for example. Conditions for color development are different depending on the label enzyme and a substrate thereof. For example, color development is carried out by leaving the products to be reacted at a temperature between 20° C. and 37° C. for an appropriate period of time.

In the second embodiment of the present invention, an anti-hapten antibody is not labeled, and detection is carried out using a labeled antibody against the anti-hapten antibody. The reaction between the anti-hapten antibody (a primary antibody) and the labeled antibody (a secondary antibody) can be carried out in a medium such as Tris buffer solution (pH 7.5) at a temperature between 20° C. and 37° C. for 15 to 60 minutes.

Subsequently, a solid carrier is washed with a washing solution such as Tris buffer solution (pH 7.5), so as to remove an unreacted labeled antibody (the secondary antibody). Thereafter, if a label for the secondary antibody is an enzyme, the enzyme is allowed to react with a color substrate, so that color development is carried out. Color development in this case may be carried out in the same manner as in the case of the first embodiment.

In the present invention, detection of a target substance or probe antibody can be carried out by the luminescence method, the fluorescence method, the delayed fluorescence method, the calorimetric method, or the electrochemical method.

The luminescence method and the fluorescence method can be carried out using, as a label, a chemoluminescent substance, fluorescent substance, or enzyme catalyzing a luminescence reaction or fluorescence reaction.

In the delayed fluorescence method, fluorescent dye having an extremely long life time of fluorescence (for example, a lanthanide chelate compound) is used. The use of such fluorescent dye having an extremely long life time of fluorescence suppresses an increase in background caused by excitation light or a short-lived fluorescent substance, resulting in the possibility of designing a high-sensitive detection system.

In the colorimetric method, a change in the absorbance of a product generated as a result of an enzyme reaction is measured. A representative example may be an enzyme peroxidase substrate ABTS (2,2'-azinobis[3-ethylbenzothiazoline-6-sulfonic acid]-diammonium salt) system.

Moreover, the use of a ferrocene derivative enables detection of a target substance by the electrochemical method.

Specific examples of a case to which the method of the present invention is applied may include, but are not limited to:
(1) protein chip;
(2) immobilized whole cell, immobilized tissue-coated sample, and staining reaction;
(3) Western blotting analysis;
(4) hemanalysis; and
(5) analysis of environmental pollutants.

The present invention will be further specifically described in the following examples. However, the examples are not intended to limit the scope of the present invention.

EXAMPLES

Synthetic Example 1

Synthesis of Theophylline-LC Derivative (1)

1 mg of theophylline-8-butanoic acid (Sigma) was dissolved in 2 ml of a 0.1 M MES buffer solution. Thereafter, 3.6 mg of WSC hydrochloride and 2.5 mg of NHS were added thereto, and the mixture was stirred at room temperature for 15 minutes. Thereafter, 2.0 mg of $\epsilon$ Amino Caproic Acid (Sigma) was dissolved in 200 µl of 0.1 M MES, and the obtained solution was added to the above reaction product. The obtained mixture was reacted at room temperature for 2 hours. 100 µl of 1M Tris buffer solution (pH 7.5) was added to the mixture, and the reaction was terminated. Thereafter, the obtained reaction product was adsorbed to a column filled with 8 g of ODS silica (YMC-ODS-AQ 120A), followed by elution with a 30% methanol aqueous solution. The eluant was concentrated and then purified by medium-pressure separation chromatography (YAMAZEN Ultrapack ODS-S-4OB).

Synthetic Example 2

Synthesis of Theophylline-BSA and Production of Antibody 2 mg of theophylline-8-butanoic acid (Sigma) was dissolved in 4 ml of 0.1 M MES buffer solution. Thereafter, 7 mg of WSC hydrochloride and 5 mg of NHS were added thereto, and the mixture was stirred at room temperature for 15 minutes. Thereafter, 10 mg of BSA (Sigma) was dissolved in 2 ml of 0.1 M MES, and the obtained solution was added to the above reaction product. The obtained mixture was reacted at room temperature for 2 hours. 500 µl of a 1M Tris buffer solution (pH 7.5) was added to the mixture, and the reaction was terminated. Thereafter, dialysis was carried out against 0.1 M Tris buffer solution (pH 7.5).

Using the theophylline-BSA as an immunogen, a mouse monoclonal antibody was produced by an ordinary method (A Laboratory Manual: Antibodies Cold Spring Harbor Laboratory, 1988).

Synthetic Example 3

Synthesis and Production of Theophylline-anti-human IgG Antibody

The theophpylline-LC derivative (0.2 mg) produced in Synthetic example 1 was dissolved in 0.4 ml of PBS. Thereafter, 0.7 mg of WSC hydrochloride and 0.5 mg of NHS were added thereto, and the mixture was stirred at room temperature for 15 minutes. Thereafter, 1 mg of an anti-human IgG antibody was dissolved in 0.2 ml of PBS, and the obtained solution was added to the above reaction product. The obtained mixture was reacted at room temperature for 2 hours. 500 µl of a 1M Tris buffer solution (pH 7.5) was added to the mixture, and the reaction was terminated. Thereafter, dialysis was carried out against 0.1 M Tris buffer solution (pH 7.5).

Synthetic Example 4

Production of Anti-theophylline Antibody ALP Conjugate

The anti-theophylline monoclonal antibody produced in Synthetic example 2 was purified by Protein A column, and then treated with papain, so as to produce F(ab')$_2$. In addition, ALP (alkaline phosphatase (Sigma)) was allowed to react with sulfosuccimidyl-4-[N-maleimidomethyl]-cyclohexane-1-carboxylate (Pierce), so that a maleimido group was introduced into the ALP. The obtained product was then allowed to react with an SH group of Fab', so as to produce an anti-theophylline antibody ALP conjugate. Detailed synthetic conditions were determined according to the method described in *Koso Meneki Sokutei Ho* (Enzyme Immunoassay), 3$^{rd}$ edition, Igaku-Shoin Ltd., 1978.

Synthetic Example 5

Synthesis and Production of Digoxigenin-anti-human IgG Antibody

20 μl of DMSO solution containing digoxigenin-NHS (Roche Diagnostics) (1 mg/20 μl) was added to 1 ml of PBS solution containing an anti-human IgG antibody (1 mg/ml), and the mixture was reacted at room temperature for 2 hours. Thereafter, 500 μl of 1 M Tris buffer solution (pH 7.5) was added thereto, and the reaction was terminated. Thereafter, dialysis was carried out against 0.1 M Tris buffer solution (pH 7.5).

Example 1

Dot Blotting

1 μl of PBS solution of human IgG was spotted on a nylon membrane followed by air-drying. Thereafter, blocking was carried out for 3 hours with 3% BSA solution.

Subsequently, the membrane was shaken at 37° C. for 30 minutes in 5 ml of a solution containing 0.5% BSA and the theophylline-anti-human IgG antibody described in Synthetic example 3. The membrane was then washed with PBS containing 0.3% Tween 20 for 10 minutes×3 times.

Thereafter, the membrane was shaken 37° C. for 30 minutes in 5 ml of a buffer solution A containing 0.5% BSA and the anti-theophylline antibody ALP conjugate described in Synthetic example 4. The membrane was then washed with Tris-HCl (pH 7.5) (1 mM MgCl$_2$, 0.1 mM ZnCl$_2$) buffer solution A containing 0.3% Tween 20 for 10 minutes×3 times. The thus obtained membrane was placed on a wrap film, and a sufficient amount of CDP-Star detection reagent attached with a CDP-Star detection kit (Roche Diagnostics) was added dropwise thereto. Three minutes later, it was wrapped in the wrap, and luminescence was detected and recorded with LAS1000 (manufactured by Fuji Photo Film Co., Ltd.).

Comparative Example 1

The same experiment as in Example 1 was carried out with the exception that the digoxigenin-anti-human IgG antibody synthesized in Synthetic example 5 was used instead of the theophylline-anti-human IgG antibody used in Example 1, and that an anti-digoxigenin antibody ALP conjugate (manufactured by Roche Diagnostics) was used instead of the anti-theophylline antibody ALP conjugate used in Example 1. This experiment was defined as a comparative example.

TABLE 1

|  | Example 1 | Comparative example 1 |
|---|---|---|
| Antibody 1 | Theophylline-anti-human IgG antibody (Synthetic example 3) | Digoxigenin-anti-human IgG antibody (Synthetic example 5) |
| Antibody 2 | Anti-theophylline antibody ALP conjugate (Synthetic example 4) | Anti-digoxigenin antibody ALP Conjugate |

(Results)

The measurement results of luminescence intensity in Example 1 and Comparative example 1 are shown in Table 2 indicated below. As is clear from the results in Table 2, a better signal was obtained in the case of using the method of the present invention than the case of using the conventional digoxigenin labeling method, and a protein placed on a membrane can be detected more efficiently in the present invention.

TABLE 2

Comparison of luminescence intensity

| Human IgG concentration | Example 1 | Comparative example 1 |
|---|---|---|
| 0 pg/μl | 1,260 | 1,300 |
| 1 pg/μl | 2,600 | 1,290 |
| 5 pg/μl | 7,240 | 1,890 |
| 25 pg/μl | 28,450 | 6,500 |
| 125 pg/μl | 103,560 | 32,300 |

EFFECTS OF THE INVENTION

The present invention can provide a method for detecting a protein using a nonradioactive marker, which is prevented to a smaller extent than in the case of the interaction of biotin/(strepto)avidin, and which can achieve higher detection sensitivity than that of the detection system using DIG.

The invention claimed is:

1. A method for detecting a target substance, which comprises steps of:
    (A) allowing a target substance to come into contact with a protein that binds to said target substance and that is labeled with a compound having a 6-membered ring represented by the following formula (1), so as to carry out a binding reaction; and
    (B) detecting the protein labeled with the compound having a 6-membered ring, which was bound to the target substance, by using an antibody that specifically binds to the compound having a 6-membered ring, wherein the antibody is conjugated to a detectable label,

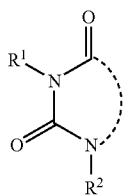

wherein R¹ and R² may be identical or different, and may independently represent a hydrogen atom, or alkyl group containing 1 to 6 carbon atoms, and the dotted line represents an atomic group necessary for forming a 6-membered ring, and wherein the compound having a 6-membered ring represented by the formula (1) is a theophylline compound.

2. A method for detecting a target substance, which comprises steps of:
(A) allowing a target substance to come into contact with a protein that binds to said target substance and that is labeled with a compound having a 6-membered ring represented by the following formula (1), so as to carry out a binding reaction;
(B) reacting the protein labeled with the compound having a 6-membered ring, which is bound to the target substance, with an antibody that specifically binds to the compound having a 6-membered ring to form a target substance-protein-antibody complex; and
(C) detecting the target substance-protein-antibody complex with a second antibody that specifically binds to the antibody in the target substance-protein-antibody complex, wherein the second antibody is conjugated to a detectable label,

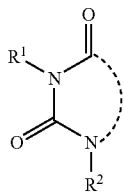

wherein R¹ and R² may be identical or different, and may independently represent a hydrogen atom, or alkyl group containing 1 to 6 carbon atoms, and the dotted line represents an atomic group necessary for forming a 6-membered ring, and wherein the compound having a 6-membered ring represented by the formula (1) is a theophylline compound.

3. method according to claim 1 or 2 wherein the target substance is immobilized on a solid phase carrier.

4. The method according to claim 1 or 2 wherein the compound having a 6-membered ring represented by the formula (1) is a compound represented by the following formula:

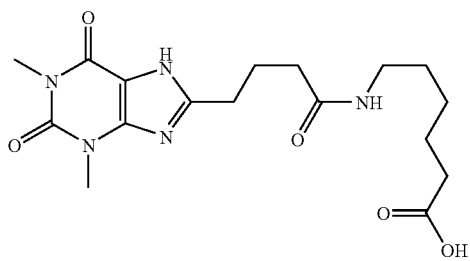

Theophylline-LC

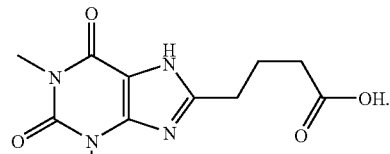

Theophylline-8-Butanoic Acid 5. method according to claim 1 or 2 wherein the antibody that specifically binds to the compound having a 6-membered ring is a monoclonal antibody.

6. The method according to claim 1 or 2 wherein the detectable label is an enzymes, a fluorescent substance, a chemiluminescent substance or a bioluminescent substance.

7. The method according to claim 6 wherein the enzyme is alkaline phosphatase, peroxidase, β-galactosidase, acetate kinase, luciferase, amylase, glucose-6-phosphate dehydrogenase, cellulase, or xanthine oxidase.

8. The method according to claim 1 or 2 wherein the detectable label is detected by luminescence, by fluorescence, by delayed fluorescence, by colorimetry or electrochemically.

9. The method according to claim 1 or 2 wherein the protein labeled with the compound having a 6-membered ring is an antibody against the target substance, a receptor, a DNA-binding protein, or a fragment thereof.

* * * * *